United States Patent
Adams et al.

(10) Patent No.: US 6,552,062 B1
(45) Date of Patent: Apr. 22, 2003

(54) INDAZOLE DERIVATIVES WITH 5-HT2 RECEPTOR ACTIVITY

(75) Inventors: David Reginald Adams, Wokingham (GB); Jonathan Mark Bentley, Wokingham (GB); Jonathan Richard Anthony Roffey, Wokingham (GB); Richard John Hamlyn, Wokingham (GB); Ashley Roger George, Wokingham (GB)

(73) Assignee: Vernalis Research Limited, Wokingham (GB)

( * ) Notice: Subject to any disclaimer, the term of this patent is extended or adjusted under 35 U.S.C. 154(b) by 0 days.

(21) Appl. No.: 09/763,886

(22) PCT Filed: Sep. 1, 1999

(86) PCT No.: PCT/GB99/02875

§ 371 (c)(1),
(2), (4) Date: Feb. 28, 2001

(87) PCT Pub. No.: WO00/12481

PCT Pub. Date: Mar. 9, 2000

(30) Foreign Application Priority Data

Sep. 1, 1998 (GB) ............................................ 98190325

(51) Int. Cl.⁷ ....................... A61K 31/416; A61P 25/24; C07D 231/56
(52) U.S. Cl. ..................................... 514/403; 548/362.5
(58) Field of Search ........................ 548/362.5; 514/403

(56) References Cited

PUBLICATIONS

May et al, "Chemical Abstracts", vol. 135, No. 257241, 2001.*

* cited by examiner

Primary Examiner—Robert W. Ramsuer
(74) Attorney, Agent, or Firm—Foley & Lardner

(57) ABSTRACT

A chemical compound of formula (I) wherein $R_1$ to $R_3$ are independently selected from hydrogen and alkyl; $R_4$ to $R_7$ are independently selected from hydrogen, halogen, hydroxy, alkyl, aryl, amino, monoalkylamino, dialkylamino, alkoxy, aryloxy, alkylthio, arylthio, arylsulfoxyl, arylsulfonyl, alkylsulfoxyl, alkylsulfonyl, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino; and $R_8$ is selected from alkyl and alkoxy, and pharmaceutically acceptable salts and prodrugs thereof, and the use thereof in therapy, particularly for the treatment of disorders of the central nervous system; damage to the central nervous system; cardiovascular disorders; gastrointestinal disorders; diabetes insipidus, and sleep apnea, and particularly for the treatment of obesity.

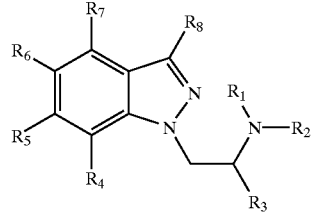

(I)

24 Claims, No Drawings

INDAZOLE DERIVATIVES WITH 5-HT2 RECEPTOR ACTIVITY

The present invention relates to indazole derivatives, to processes and intermediates for their preparation, to pharmaceutical compositions containing them and to their medicinal use. The active compounds of the present invention are useful in treating obesity and other disorders.

It has been recognised that obesity is a disease process influenced by environmental factors in which the traditional weight loss methods of dieting and exercise need to be supplemented by therapeutic products (S. Parker, "*Obesity: Trends and Treatments*", Scrip Reports, PJB Publications Ltd, 1996).

Whether someone is classified as overweight or obese is generally determined on the basis of their body mass index (BMI) which is calculated by dividing body weight (kg) by height squared (m²). Thus, the units of BMI are kg/m² and it is possible to calculate the BMI range associated with minimum mortality in each decade of life. Overweight is defined as a BMI in the range 25–30 kg/m², and obesity as a BMI greater than 30 kg/m². There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (Reductil®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective 5-HT$_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, *Psychopharmacol.*, 1988, 96, 93–100; G. A. Kennett, C. T. Dourish and G. Curzon, *Eur. J. Pharmacol.*, 1987, 141, 429–435) and to accelerate the appearance of the behavioural satiety sequence (S. J. Kitchener and C. T. Dourish, *Psychopharmacol.*, 1994, 113, 369–377). Recent findings from studies with mCPP in normal human volunteers and obese subjects have also shown decreases in food intake. Thus, a single dose of mCPP decreased food intake in female volunteers (A. E. S. Walsh et al., *Psychopharmacol.*, 1994, 116, 120–122) and decreased the appetite and body weight of obese male and female subjects during subchronic treatment for a 14 day period (P. A. Sargeant et al., *Psychopharmacol.*, 1997, 133, 309–312). The anorectic action of mCPP is absent in 5-HT$_{2C}$ receptor knockout mutant mice (L. H. Tecoft et al., *Nature*, 1995, 374, 542–546) and is antagonised by the 5-HT$_{2C}$ receptor antagonist SB-242084 in rats (G. A. Kennett et al., *Neuropharmacol.*, 1997, 36, 609–620). It seems therefore that mCPP decreases food intake via an agonist action at the 5-HT$_{2C}$ receptor.

Other compounds which have been proposed as 5-HT$_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to 5-HT$_{2C}$ receptors and may be used in the treatment of obesity. WO-A-98/30548 discloses aminoalkylindazole compounds as 5-HT$_{2C}$ agonists for the treatment of CNS diseases and appetite regulation disorders.

It is an object of this invention to provide selective, directly acting 5HT$_2$ receptor ligands for use in therapy and particularly for use as anti-obesity agents. It is a further object of this invention to provide directly acting ligands selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands, preferably 5-HT$_{2C}$ receptor agonists, for use in therapy and particularly for use as anti-obesity agents.

According to the present invention there is provided a chemical compound of formula (I):

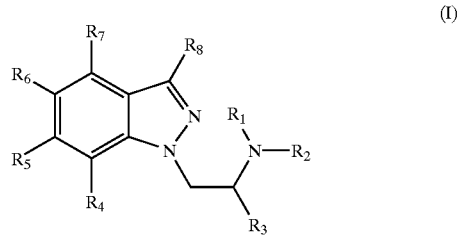

(I)

wherein:

$R_1$ to $R_3$ are independently selected from hydrogen and alkyl;

$R_4$ to $R_7$ are independently selected from hydrogen, halogen, hydroxy, alkyl, aryl, amino, monoalkylamino, dialkylamino, alkoxy, aryloxy, alkylthio, arylthio, arylsulfoxyl, arylsulfonyl, alkylsulfoxyl, alkylsulfonyl, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino; and $R_8$ is selected from alkyl and alkoxy, and pharmaceutically acceptable salts and prodrugs thereof.

As used herein, the term "alkyl" means a branched or unbranched, cyclic or acyclic, saturated or unsaturated (e.g. alkenyl or alkynyl) hydrocarbyl radical. Where cyclic, the alkyl group is preferably $C_3$ to $C_{12}$, more preferably $C_5$ to $C_{10}$, more preferably $C_5$, $C_6$ or $C_7$. Where acyclic, the alkyl group is preferably $C_1$ to $C_{10}$, more preferably $C_1$ to $C_6$, more preferably methyl, ethyl, propyl (n-propyl or isopropyl) or butyl (n-butyl, isobutyl or tertiary-butyl), more preferably methyl.

As used herein, the term "lower alkyl" means methyl, ethyl, propyl (n-propyl or isopropyl) or butyl (n-butyl, isobutyl or tertiary-butyl).

As used herein, the term "aryl" means an aromatic group, such as phenyl or naphthyl, or a heteroaromatic group containing one or more, preferably one, heteroatom, such as pyridyl, pyrrolyl, furanyl and thienyl.

The alkyl and aryl groups may be substituted or unsubstituted. Where substituted, there will generally be 1 to 3 substituents present, preferably 1 substituent. Substituents may include:

carbon-containing groups such as
  alkyl,
  aryl,
  arylalkyl (e.g. substituted and unsubstituted phenyl, substituted
  and unsubstituted benzyl);
halogen atoms and halogen-containing groups such as
  haloalkyl (e.g. trifluoromethyl);
oxygen-containing groups such as
  alcohols (e.g. hydroxy, hydroxyalkyl, aryl(hydroxy)alkyl),
  ethers (e.g. alkoxy, aryloxy, alkoxyalkyl, aryloxyalkyl),
  aldehydes (e.g. carboxaldehyde),
  ketones (e.g. alkylcarbonyl, alkylcarbonylalkyl, arylcarbonyl, arylalkylcarbonyl, arylcarbonylalkyl),
  acids (e.g. carboxy, carboxyalkyl),
  acid derivatives such as esters (e.g. alkoxycarbonyl, alkoxycarbonylalkyl, alkylcarbonyloxy, alkylcarbonyloxyalkyl),
  amides (e.g. aminocarbonyl, mono- or di-alkylaminocarbonyl, aminocarbonylalkyl, mono- or di-alkylaminocarbonylalkyl, arylaminocarbonyl),
  carbamates (e.g. alkoxycarbonylamino, aryloxycarbonylamino, aminocarbonyloxy, mono- or di-alkylaminocarbonyloxy, arylaminocarbonyloxy)
  and ureas (e.g. mono- or di-alkylaminocarbonylamino or arylaminocarbonylamino);
nitrogen-containing groups such as
  amines (e.g. amino, mono- or di-alkylamino, aminoalkyl, mono- or di-alkylaminoalkyl),
  azides,
  nitriles (e.g. cyano, cyanoalkyl),
  nitro;
sulfur-containing groups such as
  thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl);
and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

As used herein, the term "alkoxy" means alkyl-O— and "alkoyl" means alkyl-CO—. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical, and more preferably a fluorine or chlorine radical.

As used herein the term "prodrug" means any pharmaceutically acceptable prodrug of the compound of formula (I).

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, succinic, phosphoric, sulfuric and methanesulfonic acids. Acceptable base salts include alkali metal (e.g. sodium, potassium), alkaline earth metal (e.g. calcium, magnesium) and aluminium salts.

Preferably, the compounds of formula (I) are selected from compounds in which $R_1$ is the same as $R_2$. Preferably, $R_1$ and $R_2$ are both hydrogen.

In an embodiment of the present invention, $R_1$ is hydrogen and $R_2$ is alkyl, preferably lower alkyl, preferably methyl. In a further embodiment, $R_1$ is hydrogen and $R_2$ is arylalkyl, preferably arylmethyl. Where $R_2$ is arylalkyl, it is preferred that said aryl substituent is a substituted or unsubstituted phenyl or thienyl group.

Preferably, the compounds of formula (I) are selected from compounds in which $R_3$ is alkyl, preferably lower alkyl, preferably methyl. Where $R_3$ is alkyl, the carbon atom to which $R_3$ is attached is an asymmetric carbon atom. It is preferred that this asymmetric carbon is in the (S)-configuration, wherein the stereochemical assignment is defined with respect to a compound wherein $R_3$ is an unsubstituted alkyl group.

$R_4$ to $R_7$ are independently selected from hydrogen, halogen, hydroxy, alkyl (including cycloalkyl, halo-alkyl (such as trifluoromethyl) and arylalkyl), aryl, amino, monoalkylamino, dialkylamino, alkoxy (including arylalkoxy), aryloxy, alkylthio, arylthio, arylsulfoxyl, arylsulfonyl, alkylsulfoxyl, alkylsulfonyl, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamnino and dialkylaminocarbonylamino.

In one embodiment of the invention $R_4$ to $R_7$ are independently selected from hydrogen, halogen, hydroxy, alkyl (including cycloalkyl, halo-alkyl (such as trifluoromethyl) and arylalkyl), aryl, alkoxy (including arylalkoxy), aryloxy, alkylthio, alkylsulfoxyl and alkylsulfonyl.

Preferably, the compounds of formula (I) are selected from compounds in which one or more of $R_4$, $R_5$, $R_6$ and $R_7$ is/are hydrogen. Preferably, one or both of $R_4$ and $R_7$ are hydrogen.

In a preferred embodiment of the invention, one or more, preferably one or two, of $R_4$, $R_5$, $R_6$ and $R_7$ are selected from halogen, preferably fluoro, chloro and bromo. Preferably one or both of $R_5$ and $R_6$ are selected from halogen.

In an alternative preferred embodiment, $R_5$ is selected from halogen, alkoxy (preferably lower alkoxy), alkylthio (preferably lower alkylthio) and alkyl (preferably trifluoromethyl).

In a further alternative preferred embodiment, $R_6$ is selected from hydrogen and halogen (preferably fluoro).

Preferably, the compounds of formula (I) are selected from compounds in which $R_8$ is alkyl, preferably methyl or ethyl, more preferably ethyl.

In a preferred embodiment of the invention, the compounds of formula (I) are selected from 1-(6-methoxy-3-methylindazol-1-yl)-2-propylamine, 1-(5,6-difluoro-3-methylindazol-1-yl)-2-propylamine, 1-(6-chloro-5-fluoro-3-methylindazol-1-yl)-2-propylamine, 1-(3-ethyl-6-trifluoromethylindazol-1-yl)-2-propylamine, 1-(6-bromo-3-ethylindazol-1-yl)-2-propylamine and 1-(3-ethyl-6-methylthioindazol-1-yl)-2-propylamine. 1-(3-Ethyl-6-methylthioindazol-1-yl)-2-propylamine and 1-(6-bromo-3-ethylindazol-1-yl)-2-propylamine are particularly preferred. It is preferred that the compounds are the (S)-enantiomers thereof. Where the compounds of formula (I) are in salt form, the fumarate salt is particularly preferred.

The compounds of the invention may contain one or more asymmetric carbon atoms, so that the compounds can exist in different stereoisomeric forms. The compounds can be, for example, racemates or optically active forms. The optically active forms can be obtained by resolution of the racemates or by asymmetric synthesis.

In a preferred embodiment of the invention, a compound of formula (I) is in the form of its (S)-enantiomer, substantially free of its (R)-enantiomer. As used herein, the term "substantially free of its (R)-enantiomer" means that a composition comprising a compound of formula (I) contains a greater proportion of the (S)-enantiomer of the compound of formula (I) in relation to the (R)-enantiomer of the compound of formula (I). In a preferred embodiment of the present invention, the term "substantially free of its (R)-enantiomer", as used herein, means that the composition contains at least 90% by weight of the (S)-enantiomer and 10% by weight or less of the (R)-enantiomer. In a further preferred embodiment, the term "substantially free of its (R)-enantiomer" means that the composition contains at least 99% by weight of the (S)-enantiomer and 1% or less of the (R)-enantiomer. In another preferred embodiment, the term "substantially free of its (R)-enantiomer" means that the composition contains 100% by weight of the (S)-enantiomer. The above percentages are based on the total amount of a compound of formula (I) present in the composition.

According to a further aspect of the invention, there is provided a compound of formula (I) for use in therapy.

The compounds of formula (I) may be used in the treatment (including prophylactic treatment) of disorders associated with 5-HT$_2$ receptor function. The compounds may act as receptor agonists or antagonists. Preferably, the compounds may be used in the treatment (including prophylactic treatment) of disorders associated with 5-HT$_{2B}$ and/or 5-HT$_{2C}$ receptor function. Preferably, the compounds may be used in the treatment (including prophylactic treatment) of disorders where a 5-HT$_{2C}$ receptor agonist is required.

The compounds of formula (I) may be used in the treatment or prevention of central nervous disorders such as depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, obesity, bulimia, anorexia nervosa or premenstrual tension; damage of the central nervous system such as by trauma, stroke, neurodegenerative diseases or toxic or infective CNS diseases such as encephalitis or meningitis; cardiovascular disorders such as thrombosis; gastrointestinal disorders such as dysfunction of gastrointestinal motility; diabetes insipidus; and sleep apnea.

According to a further aspect of the invention, there is provided use of a compound of formula (I) in the manufacture of a medicament for the treatment (including prophylaxis) of the above-mentioned disorders. In a preferred embodiment, there is provided use of a compound of formula (I) in the manufacture of a medicament for the treatment (including prophylaxis) of obesity.

According to a further aspect of the invention, there is provided a method of treatment (including prophylaxis) of a disorder selected from the group consisting of the above-mentioned disorders comprising administering to a patient in need of such treatment an effective dose of a compound of formula (I). In a preferred embodiment, there is provided a method of treatment (including prophylaxis) of obesity.

According to a further aspect of the invention, there is provided a pharmaceutical composition comprising a compound of formula (I) in combination with a pharmaceutically acceptable carrier or excipient and a method of making such a composition comprising combining a compound of formula (I) with a pharmaceutically acceptable carrier or excipient.

According to a further aspect of the invention, there is provided a method of preparing a compound of formula (I).

Compounds of the invention may be prepared according to Reaction Scheme 1. $R_1$ to $R_8$ are as previously defined. The (indazolyl)-alkylethanol (III) may be prepared by reaction of the substituted indazole (II) with an alkylene oxide in the presence of a strong base such as sodium hydride in a solvent such as tetrahydrofuran. The corresponding azido derivative (V) can be formed in a two step procedure from the derivative (III) by formation of the mesylate (IV), obtained by reaction of (III) with methanesulfonyl chloride in the presence of a base such as triethylamine, and subsequent treatment of the mesylate (IV) with sodium azide in a solvent such as dimethyl formamide. The azidoindazole (V) can then be reduced to a compound of formula (I) ($R_1=R_2=$H) using for example a mixture of zinc powder and nickel chloride hexahydrate in a solvent such as tetrahydrofuran. The compounds of formula (I) ($R_1$ and/or $R_2$=alkyl) may be prepared by standard methods such as reductive alkylation of compound (I) ($R_1=R_2=$H) with an appropriate aldehyde or ketone in the presence of a reducing agent such as sodium triacetoxyborohydride, formic acid or sodium cyanoborohydride.

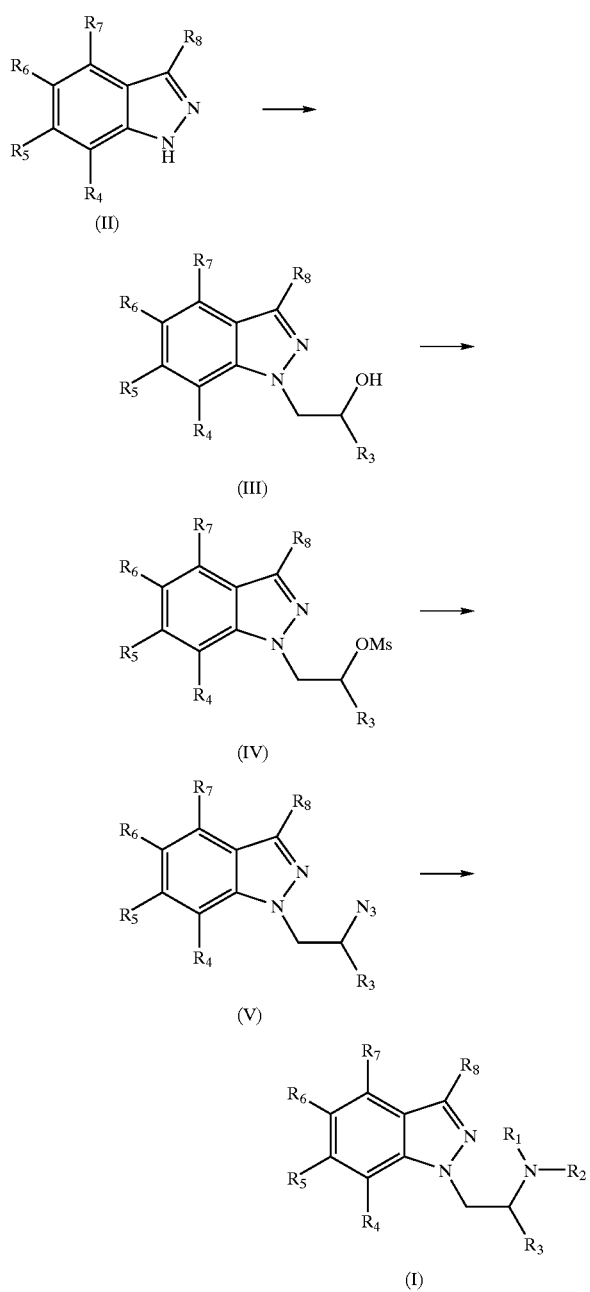

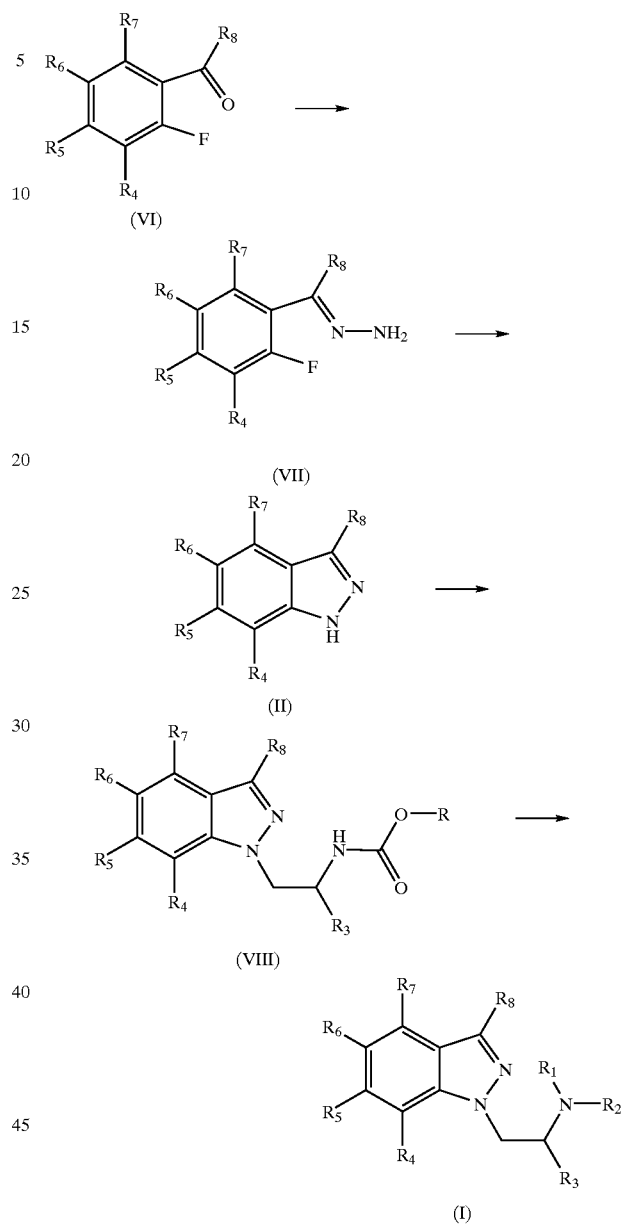

Alternatively, compounds of the invention may be prepared according to Reaction Scheme 2. $R_1$ to $R_8$ are as previously defined. The hydrazone (VII) may be prepared by reaction of the alkyl-aryl ketone (VI) with hydrazine. The indazole (II) can be formed from the hydrazone (VII) by thermally-induced cyclisation with elimination of hydrogen fluoride. The carbamate (VIII) may be formed by reaction of the indazole (II) with a 2-carbamylethylsulfonate in the presence of a strong base such as potassium hydroxide in a solvent such as methyl sulfoxide. The indazole-2-alkylamine (I) ($R_1=R_2=H$) may be obtained by reaction of the carbamate (VIII) with a reagent suitable to reveal the protected amine function.

If, in any of the other processes mentioned herein, the substituent group $R_4$, $R_5$, $R_6$, $R_7$ or $R_8$ is other than the one required, the substituent group may be converted to the desired substituent by known methods. The substituents $R_4$, $R_5$, $R_6$, $R_7$ or $R_8$ may also need protecting against the conditions under which the reaction is carried out. In such a case, the protecting group may be removed after the reaction has been completed.

The processes described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate, talc or silica); disintegrants (e.g. potato starch or sodium starch glycollate); or wetting agents (e.g. sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

EXPERIMENTAL

Assay Procedures

1. Binding to Serotonin Receptors

The binding of compounds of formula I to serotonin receptors was determined in vitro by standard methods. The preparations were investigated in accordance with the assays given hereinafter.

Method (a): For the binding to the $5\text{-HT}_{2C}$ receptor the $5\text{-HT}_{2C}$ receptors were radiolabeled with $[^3H]$-5-HT. The affinity of the compounds for $5\text{-HT}_{2C}$ receptors in a CHO cell line was determined according to the procedure of D. Hoyer, G. Engel and H. O. Kalkman, *European J Pharmacol.*, 1985, 118, 13–23.

Method (b): For the binding to the $5\text{-HT}_{2B}$ receptor the $5\text{-HT}_{2B}$ receptors were radiolabeled with $[^3H]$-5-HT. The affinity of the compounds for human $5\text{-HT}_{2B}$ receptors in a CHO cell line was determined according to the procedure of K. Schmuck, C. Ullmer, P. Engels and H. Lubbert, *FEBS Lett.*, 1994, 342, 85–90.

The thus determined activity of compounds of formula (I) is shown in Table 1.

TABLE 1

| Compound | Method (a) $K_i$ (2C) | Method (b) $K_i$ (2B) |
| --- | --- | --- |
| Example 1 | 431 nM | 241 nM |
| Example 2 | 210 nM | 135 nM |
| Example 3 | 140 nM | 63 nM |
| Example 4 | 75 nM | 26 nM |
| Example 8 | 37 nM | 47 nM |

2. Functional Activity

The functional activity of compounds of formula (I) was assayed using a Fluorimetric Imaging Plate reader (FLIPR). CHO cells expressing the human $5\text{-HT}_{2C}$ or human $5\text{-HT}_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 µL/well of assay buffer (Hanks balanced salt solution containing 20 mM Hepes and 2.5 mM probenecid). The drug (dissolved in 50 µL of the assay buffer) was added at a rate of 70 µL/sec to each well of the FLIPR 96 well plate during fluorescence measurements. The measurements were taken at 1 sec intervals and the maximum fluorescent signal was measured (approx 10–15 secs after drug addition) and compared with the response produced by 10 µM 5-HT (defined as 100%) to which it was expressed as a percentage response (relative efficacy). Dose response curves were constructed using Graphpad Prism (Graph Software Inc.).

The thus determined activity of compounds of formula (I) is shown in Table 2.

TABLE 2

| Compound | h5-HT$_{2A}$ EC$_{50}$ (nM) | Relative Efficacy (%) | h5-HT$_{2C}$ EC$_{50}$ (nM) | Relative Efficacy (%) |
|---|---|---|---|---|
| Example 1 | — | — | 960 | 55 |
| Example 2 | 108 | 59 | 44 | 74 |
| Example 3 | 152 | 50 | 84 | 67 |
| Example 4 | 137 | 65 | 48 | 76 |
| Example 5 | — | — | 877 | 73 |
| Example 6 | 288 | 32 | 52 | 47 |
| Example 7 | 739 | 39 | 88 | 69 |
| Example 8 | 285 | 48 | 8 | 81 |

SYNTHETIC EXAMPLES

Example 1

(RS)-1-(3-Methylindazol-1-yl)-2-propylamine Fumarate

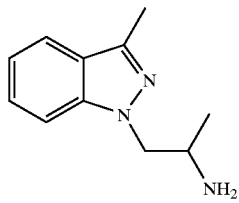

(RS)-1-[2-(tert-Butoxycarbonylamino)propyl]-3-methylindazole

3-Methyl-1H-indazole (1.0 g, 7.6 mmol) was added portionwise to a stirred mixture of methyl sulfoxide (25 ml) and powdered potassium hydroxide (85%, 1.5 g, 26.6 mmol). The mixture was warmed to 35° C. and left to stir for 30 min. A mixture of (RS)-2-(tert-butoxycarbonylamino)propane methanesulfonate (4.9 g, 19.4 mmol) in methyl sulfoxide (10 mL) was added over 2 h, the mixture was then left to stir at 35° C. for 20 h. Water (20 mL) was added and the mixture was extracted with ether (3×20 mL). The combined organic extracts were washed with brine (2×), dried (magnesium sulfate), concentrated in vacuo and purified by column chromatography [SiO$_2$; heptane-ethyl acetate (5:1)] to give the product (1.2 g, 51% yield) as a pale yellow solid: IR $v_{max}$ (Nujol/cm$^{-1}$) 3368, 1683, 1536, 1461, 1370, 1249, 1170, 1059, and 743; NMR $\delta_H$ (400 MHz, CDCl$_3$) 1.13 (3H, d, J 6.5 Hz), 1.41 (9H, s), 2.57 (3H, s), 4.11 (1H, m), 4.28–4.48 (2H, m), 4.85 (1H, br s), 7.08–7.14 (1H, m), 7.33–7.46 (2H, m) and 7.64 (1H, d, J 8 Hz).

(RS)-1-(3-Methylindazol-1-yl)-2-propylamine Fumarate

A mixture of (RS)-1-[2-(tert-butoxycarbonylamino) propyl]-3-methylindazole (1.2 g, 4.3 mmol), dichloromethane (15 mL) and trifluoroacetic acid (5 mL) was stirred for 1 h. The mixture was partitioned between aqueous sodium hydroxide solution (2 N, 30 mL) and dichloromethane (3×30 mL). The combined organic extracts were washed with brine (2×), dried (magnesium sulfate) and concentrated in vacuo to give an orange oil. 2-Propanol (5 mL) was added, the mixture was heated to boiling, then fumaric acid (0.5 g, 4.3 mmol) was added. The mixture was cooled to room temperature and filtered. The filter cake was dried in vacuo to give the title compound (0.89 g, 68%) as a pale brown solid: mp 145–147° C.; IR $v_{max}$ (Nujol/cm$^{-1}$) 1618, 1510, 1458, 1377, 973, 742 and 652; NMR $\delta_H$ (400 MHz, DMSO-d$_6$) 1.09 (3H, d, J 6.5 Hz), 2.49 (3H, s), 3.56 (1H, m), 4.39 (2H, m), 6.47, (2H, s), 7.09–7.15 (1H, m), 7.36–7.41 (1H, m), 7.62 (1H, d, J 8 Hz) and 7.72 (1H, d, J 8 Hz).

Example 2

(S)-1-(6-Methoxy-3-methylindazol-1-yl)-2-propylamine Fumarate

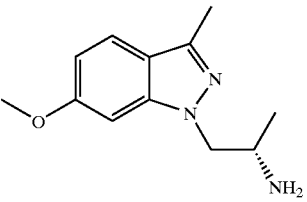

6-Methoxy-3-methyl-1H-indazole

To a stirred solution of 2'-fluoro-4'-methoxyacetophenone (0.5 g, 3.0 mmol) in ethylene glycol (10 mL) was added dropwise hydrazine hydrate (0.1 g, 3.1 mmol). The mixture was stirred for 24 h and partitioned between dichloromethane (20 mL) and water (3×20 mL). The organic layer was dried (magnesium sulfate), concentrated in vacuo and purified by column chromatography [SiO$_2$; ethyl acetate-heptane (1:1)] to give an orange oil. The oil was dissolved in ethylene glycol (10 mL) and heated at 165° C. for 24 h. The solution was cooled to room temperature and partitioned between dichloromethane (20 mL) and water (3×20 mL). The organic extract was dried (magnesium sulfate), concentrated in vacuo and purified by column chromatography [SiO$_2$; ethyl acetate-heptane (1:5)] to give the product (0.25 g, 51%) as a colourless solid: IR $v_{max}$ (Nujol/cm$^{-1}$) 1624, 1519, 1458, 1295, 1208, 1170, 1024 and 821; NMR $\delta_H$ (400 MHz, CDCl$_3$) 2.54 (3H, s), 3.86 (3H, s), 6.78–6.81 (2H, m) and 7.52 (1H, d, J 9 Hz).

(S)-1-[2-(tert-Butoxycarbonylamino)propyl]-6-methoxy-3-methylindazole (S)-1-[2-(tert-Butoxycarbonylamino)propyl]-6-methoxy-3-methylindazole was prepared from 6-methoxy-3-methyl-1H-indazole (0.19 g, 1.1 mmol) and (S)-2-(tert-butoxycarbonylamino)propane methanesulfonate according to the method described in Example 1 to give the product (0.18 g, 51% yield) as a pale orange oil: NMR $\delta_H$ (400 MHz, CDCl$_3$) 1.13 (3H, d, J 6.5 Hz), 1.41 (9H, s), 2.52 (3H, s), 3.89 (3H, s), 4.12 (1H, m), 4.26 (H, m), 4.31–4.41 (1H, m), 4.96 (1H, br s), 6.76 (1H, dd, J 2 Hz, J 6.5 Hz), 6.78–6.83 (1H, m) and 7.48 (1H, d, J 9 Hz).

(S)-1-(6-Methoxy-3-methylindazol-1-yl)-2-propylamine Fumarate (S)-1-(6-Methoxy-3-methylindazol-1-yl)-2-propylamine fumarate was prepared from (S)-1-[2-(tert-butoxycarbonylamino)propyl]-6-methoxy-3-methylindazole according to the method described in Example 1 to give the title compound (0.071 g, 62%) as a white solid: mp 180–181° C.; Found C, 56.96; H, 6.36; N, 12.45%. C$_{12}$H$_{17}$N$_3$O.C$_4$H$_4$O$_4$ requires: C, 57.30; H, 6.31; N, 12.52%; NMR $\delta_H$ (400 MHz, DMSO-d$_6$) 1.16 (3H, d, J 6.5 Hz), 2.44 (3H, s), 3.63 (1H, m), 3.85 (3H, s), 4.38 (1H, dd, J 14, 6.5 Hz), 4.51 (1H, dd, J 14, 6.5 Hz), 6.49, (2H, s), 6.74 (1H, m), 7.19 (1H, m) and 7.52 (1H, d, J 8.5 Hz).

Example 3

(S)-1-(5,6-Difluoro-3-methylindazol-1-yl)-2-propylamine Fumarate

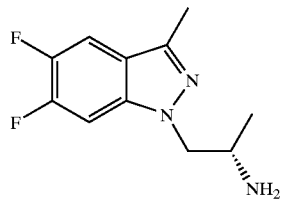

5,6-Difluoro-3-methyl-1H-indazole 5,6-Difluoro-3-methyl-1H-indazole was prepared according to the method described in Example 2 using 2',4',5'-trifluoroacetophenone (1.0 g, 5.7 mmol) to produce 0.44 g (48% yield) of the product as a white solid: IR $v_{max}$ (Nujol/cm$^{-1}$)1642, 1513, 1461, 1377, 1336, 1202, 1055 and 848; NMR $\delta_H$(400 MHz, CDCl$_3$) 2.55 (3H, s), 7.19 (1H, dd, J 4, 6 Hz) and 7.39 (1H, dd, J 2, 7.5 Hz).

(S)-1-[2-(tert-Butoxycarbonylamino)propyl]-5,6-difluoro-3-methylindazole (S)-1-[2-(tert-Butoxycarbonylamino)propyl]-5,6-difluoro-3-methylindazole was prepared according to the method described in Example 2 using 5,6-difluoro-3-methyl-1H-indazole (0.26 g, 1.6 mmol) to produce 0.28 g (57% yield) of the product as a white solid: NMR $\delta_H$ (400 MHz, CDCl$_3$) 1.13 (3H, d, J 6.5 Hz), 1.42 (9H, s), 2.51 (3H, s), 4.03 (1H, m), 4.26–4.4 (2H, m), 4.67 (1H, br s), 7.17–7.26 (1H, m) and 7.31–7.38 (1H, m).

(S)-1-(5,6-Difluoro-3-methylindazol-1-yl)-2-propylamine Fumarate (S)-1-(5,6-Difluoro-3-methylindazol-1-yl)-2-propylamine fumarate was prepared according to the method described in Example 2 using (5)-1-[2-(tert-butoxycarbonylamino)propyl]-5,6-difluoro-3-methylindazole (0.28 g, 0.9 mmol) to produce 0.16 g (51% yield) of the title compound as a white solid: mp 160–161° C.; Found C, 51.81; H, 4.94; N, 11.85%. C$_{11}$H$_{13}$F$_2$N$_3$.C$_4$H$_4$O$_4$.0.25H$_2$O requires: C, 52.10; H, 5.10; N, 12.15%; IR $v_{max}$ (Nujol/cm$^{-1}$) 1713, 1632, 1518, 1457, 1377, 972 and 848; NMR $\delta_H$ (400 MHz, DMSO-d$_6$) 1.13 (3H, d, J 6 Hz), 2.48 (3H, s), 3.51–3.62 (1H, m), 4.32–4.5 (2H, m), 6.51 (2H, s) and 7.79–7.89 (2H, m).

Example 4

(S)-1-(6-Chloro-5-fluoro-3-methylindazol-1-yl)-2-propylamine Fumarate

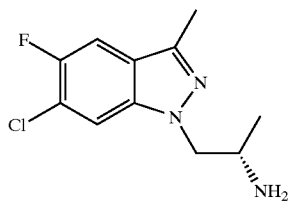

6-Chloro-5-fluoro-3-methyl-1H-indazole

6-Chloro-5-fluoro-3-methyl-1H-indazole was prepared according to the method described in Example 2 using 4'-chloro-2',5'-difluoroacetophenone (2.0 g, 10 mmol) to produce 0.83 g (45% yield) of the product as a beige solid: IR $v_{max}$ (Nujol/cm$^{-1}$) 3221, 1457, 1306, 1294, 1071, 1012 and 856; NMR $\delta_H$ (400 MHz, CDCl$_3$) 2.54 (3H, s), 7.39 (1H, d, J 9 Hz) and 7.49 (1H, d, J 5.5 Hz).

(S)-1-[2-(tert-Butoxycarbonylamino)propyl]-6-chloro-5-fluoro-3-methylindazole (S)-1-[2-(tert-Butoxycarbonylamino)propyl]-6-chloro-5-fluoro-3-methylindazole was prepared according to the method described in Example 2 using 6-chloro-5-fluoro-3-methyl-1H-indazole (0.27 g, 1.5mmol) to produce 0.28 g (62%) of the product as a beige solid: IR $v_{max}$ (Nujol/cm$^{-1}$) 3361, 1678, 1532, 1461, 1238, 1165, 1082, 860 and 638; NMR $\delta_H$ (400 MHz, CDCl$_3$) 1.16 (3H, d, J 6.5 Hz), 1.41 (9H, s), 2.52 (3H, s), 4.05 (1H, m), 4.28–4.41 (2H, m), 4.66 (1H, br s), 7.33 (1H, d, J 9 Hz) and 7.45–7.5 (1H, m).

(S)-1-(6-Chloro-5-fluoro-3-methylindazol-1-yl)-2-propylamine Fumarate (S)-1-(6-Chloro-5-fluoro-3-methylindazol-1-yl)-2-propylamine fumarate was prepared according to the method described in Example 2 using (S)-1-[2-(tert-butoxycarbonylamino)propyl]-6-chloro-5-fluoro-3-methylindazole (0.28 g, 0.9 mmol) to produce 0.19 g (61% yield) of the title compound as a white solid: mp 158–159° C.;

Found C, 50.07; H, 4.75; N, 11.43%. C$_{11}$H$_{13}$ClFN$_3$.C$_4$H$_4$O$_4$ requires: C, 50.36; H, 4.79; N, 11.74%; IR $v_{max}$ (Nujol/cm$^{-1}$) 1713, 1626, 1512, 1458, 1241, 975, 816 and 651; NMR $\delta_H$ (400 MHz, DMSO-d$_6$) 1.13 (3H, d, J 6 Hz), 2.49 (3H, s), 3.49–3.61 (1H, m), 4.33–4.52 (2H, m), 6.49 (2H, s) and 7.81 (1H, d, J 9.5 Hz) and 8.07 (1H, d, J 6 Hz).

Example 5

(S)-1-(3-Ethyl-6-trifluoromethylindazol-1-yl)-2-propylamine Fumarate

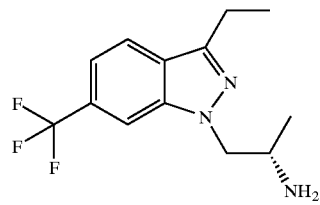

2'-Fluoro-4'-trifluoromethylphenylpropiohydrazone

To a stirred solution of 2'-fluoro-4'-trifluoromethylpropiophenone (2.0 g, 9 mmol) in ethylene glycol (20 mL) was added dropwise hydrazine hydrate (0.58 g, 0.9 mmol). The mixture was stirred for 24 h and partitioned between dichloromethane (40 mL) and water (3×20 mL). The organic layer was dried (magnesium sulfate), concentrated in vacuo and purified by column chromatography [SiO$_2$; ethyl acetate-heptane (1:5)] to give the product (1.3 g, 61%) as a colourless oil: IR $v_{max}$ (Nujol/cm$^{-1}$) 3388, 1421, 1330, 1172, 1130, 900 and 746; NMR $\delta_H$(400 MHz, CDCl$_3$) 1.10 (3H, t, J 7 Hz), 2.51 (0.6H, q, J 7.5 Hz), 2.61 (1.4H, q, 7.5 Hz), 5.06 (0.6H, br s), 5.59 (1.4H, br s), 7.29–7.55 (2.2H, m) and 7.61 (0.8H, t, J 8.5 Hz).

3-Ethyl-6-trifluoromethyl-1H-indazole

A solution of 2'-fluoro-4'-trifluoromethylphenylpropiohydrazone (1.3 g, 5.6 mmol) in ethylene glycol (50 mL) was heated at 165° C. for 24 h. The solution was cooled to room temperature and partitioned between dichloromethane (70 mL) and the solution water (3×20 mL). The organic layer was dried (magnesium sulfate), concentrated in vacuo and purified by column chromatography [SiO$_2$; ethyl acetate-heptane (1:5)] to give the product (0.5 g, 41%) as a yellow solid: IR $\nu_{max}$ (Nujol/cm$^{-1}$) 3265, 1467, 1455, 1338, 1235, 1115, 874 and 714; NMR $\delta_H$ (400 MHz, CDCl$_3$) 1.45 (3H, t, J 8 Hz), 3.07 (2H, q, J 7.5 Hz), 7.37 (1H, d, J 8.5 Hz), 7.75 (1H, s), 7.83 (1H, d, J 8.5 Hz) and 9.75 (1H, br s).

(S)-1-[2-(tert-Butoxycarbonylamino)propyl]-3-ethyl-6-trifluoromethylindazole (S)-1-[2-(tert-Butoxycarbonylamino)propyl]-3-ethyl-6-trifluoromethylindazole was prepared according to the method described in Example 2 using 3-ethyl-6-trifluoromethylindazole (0.49 g, 2.3 mmol) to produce 0.48 g (56%) of the product as a white solid: IR $\nu_{max}$ (Nujol/cm$^{-1}$) 3360, 1681, 1531, 1461, 1313, 1169, and 1120; NMR $\delta_H$ (400 MHz, CDCl$_3$) 1.16 (3H, d, J 6.5 Hz), 1.33–1.43 (12H, m), 3.01 (2H, q, J 7 Hz), 4.07–4.18 (1H, m), 4.39–4.49 (2H, m), 4.76 (1H, br s), 7.32 (1H, d, J 8 Hz) 7.71 (1H, br s) and 7.78 (1H, d, J 8.5 Hz).

(S)-1-(3-Ethyl-6-trifluoromethylindazol-1-yl)-2-propylamine Fumarate (S)-1-(3-Ethyl-6-trifluoromethylindazol-1-yl)-2-propylamine fumarate was prepared according to the method described in Example 2 using (S)-1-[2-(tert-butoxycarbonylamino)propyl]-3-ethyl-6-trifluoromethylindazole (0.3 g, 0.8 mmol) to produce 0.20 g (63% yield) of the title compound as a white solid: mp 151–153° C.; Found C, 52.34; H, 5.27; N, 10.62%. C$_{11}$H$_{13}$F$_3$N$_3$.C$_4$H$_4$O$_4$ requires: C, 52.71; H, 5.20; N, 10.85%; IR $\nu_{max}$ (Nujol/cm$^{-1}$) 1707, 1630, 1501, 1461, 1376, 1313, 1124, 1059 and 652; NMR $\delta_H$ (400 MHz, DMSO-d$_6$) 1.17 (3H, d, J 7 Hz), 1.35 (3H, t, J 7 Hz), 2.99 (2H, q, J 7.5 Hz), 3.62 (1H, m), 4.48–4.56 (1H, m), 4.59–4.68 (1H, m), 6.49 (2H, s), 7.4 (1H, d, J 8.5 Hz), 8.01 (1H, d, J 8.5 Hz) and 8.22 (1H, s).

Example 6

(S)-1-(3-Ethyl-6-fluoroindazol-1-yl)-2-propylamine Fumarate

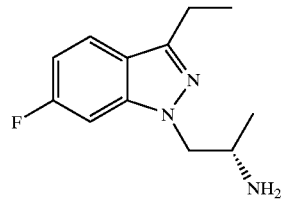

2',4'-Difluorophenylpropiohydrazone

2',4'-Difluorophenylpropiohydrazone was prepared according to the method described in Example 5 using 2',4'-difluoropropiophenone (5.0 g, 30 mmol) to produce 2.6 g (48%) of the product as a colourless oil: IR $\nu_{max}$ (Nujol/cm$^{-1}$) 3385, 1614, 1502, 1420, 1267, 1140, 968 and 850; NMR $\delta_H$ (400 MHz, CDCl$_3$) 1.03–1.15 (3H, m), 2.48 (0.7H, q, J 7.5 Hz), 2.58 (1.3H, q, J 7.5 Hz), 5.04 (0.7H, br s), 5.46 (1.3H, br s), 6.76–7.01 (2H, m), 7.16–7.23 (0.4H, m) and 7.4–7.47 (0.6H, m).

3-Ethyl-6-fluoro-1H-indazole

3-Ethyl-6-fluoro-1H-indazole was prepared according to the method described in Example 5 using 2',4'-difluorophenylpropiohydrazone (3.5 g, 19 mmol) to produce 1.7 g (53%) of the product as a white solid: IR $\nu_{max}$ (Nujol/cm$^{-1}$) 3168, 1633, 1350, 1230, 1153, 1124, 1041 and 838; NMR $\delta_H$ (400 MHz, CDCl$_3$) 1.42 (3H, t, J 7.5 Hz), 3.01 (2H, q, J 8 Hz), 6.91 (1H, m), 7.08 (1H, dd, J 2, 9.5 Hz), 7.65 (1H, dd, J 5.5, 9 Hz) and 9.12 (1H, br s).

(S)-1-[2-(tert-Butoxycarbonylamino)propyl]-3-ethyl-6-fluoroindazole (S)-1-[2-(tert-Butoxycarbonylamino)propyl]-3-ethyl-6-fluoroindazole was prepared according to the method described in Example 2 using 3-ethyl-6-fluoro-1H-indazole (1.5 g, 9 mmol) to produce 1.47 g (51%) of the product as a white solid: IR $\nu_{max}$ (Nujol/cm$^{-1}$), 3363, 1677, 1534, 1463, 1368, 1267, 1161, 1066 and 844; NMR $\delta_H$ (400 MHz, CDCl$_3$) 1.15 (3H, d, J 7 Hz), 1.34–1.44 (12H, m), 2.96 (2H, q, J 7.5 Hz), 4.06 (1H, m), 4.31–4.37 (2H, m), 4.79 (1H, br s), 6.87 (1H, m), 7.06 (1H, d, J 9.5 Hz) and 7.59 (1H, m).

(S)-1-(3-Ethyl-6-fluoroindazol-1-yl)-2-propylamine Fumarate (S)-1-(3-Ethyl-6-fluoroindazol-1-yl)-2-propylamine fumarate was prepared according to the method described in Example 2 using (S)-1-[2-(tert-butoxycarbonylamino) propyl]-3-ethyl-6-fluoroindazole (0.9 g, 2.8 mmol) to produce 0.5 g (54% yield) of the title compound as a colourless solid: mp 143–145° C.; IR $\nu_{max}$ (Nujol/cm$^{-1}$) 1702, 1627, 1461, 1377, 1124, 972, and 652; NMR $\delta_H$ (400 MHz, DMSO-d$_6$) 1.13 (3H, d, J 6.5 Hz), 1.32 (3H, t, J 7.5 Hz), 1.43 (2H, q, J 7.5 Hz), 3.59 (1H, m), 4.34–4.51 (2H, m), 6.49 (2H, s), 6.95–7.03 (1H, m), 7.56 (1H, dd, J 2, 10 Hz) and 7.8 (1H, dd, J 5, 8.5 Hz).

Example 7

(S)-1-(6-Bromo-3-ethylindazol-1-yl)-2-propylamine Fumarate

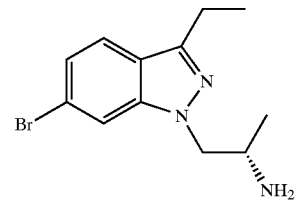

4'-Bromo-2'-fluoropropiophenone

A mixture of 3-fluorobromobenzene (5.0 g, 29 mmol) and aluminium (III) chloride (11.6 g, 87 mmol) was heated under argon until a slurry formed. Propionyl chloride (3.2 g, 35 mmol) was added over 15 min and the mixture was heated at 90° C. for 1 h. The reaction was poured onto ice-water (100 mL) and the resultant mixture was extracted with dichloromethane (3×50 mL). The combined organic extracts were dried (magnesium sulfate), concentrated in vacuo and purified by column chromatography (SiO$_2$; heptane) to give the product (1.2 g, 18%) as a colourless oil: NMR $\delta_H$ (400 MHz, CDCl$_3$) 1.18 (3H, t, J 7.5), 2.95 (2H, m), 7.29–7.38 (2H, m) and 7.75 (1H, t, J 8 Hz).

4'-Bromo-2'-fluorophenylpropiohydrazone

4'-Bromo-2'-fluorophenylpropiohydrazone was prepared according to the method described in Example 5 using 4'-bromo-2'-fluoropropiophenone (0.67 g, 3.0 mmol) to produce 0.23 g (32%) of the product as a yellow oil: NMR $\delta_H$ (400 MHz, CDCl$_3$) 1.03–1.14 (3H, m), 2.47 (0.6H, q, J 7.5 Hz), 2.57 (1.4H, q, J 7.5), 5.04 (0.6H, br s), 5.49 (1.4H, br s), 7.09 (0.3H, t, J 8 Hz), 7.2–7.3 (1.4H, m) and 7.32–7.42 (1.4H, m).

6-Bromo-3-ethylindazole

6-Bromo-3-ethylindazole was prepared according to the method described in Example 5 using 4'-bromo-2'-fluorophenylpropiohydrazone (0.6 g, 2.5 mmol) to produce 0.3 g (54%) of the product as a white solid: IR $v_{max}$ (Nujol/cm$^{-1}$) 3204, 1616, 1461, 1377, 1340, 1036 and 800; NMR $\delta_H$ (400 MHz, CDCl$_3$) 1.42 (3H, t, J 7.5 Hz), 3.01 (2H, q, J 7.5 Hz), 7.23–7.27 (1H, m), 7.57 (1H, d, J 8.5 Hz) and 7.62 (1H, br s).

(S)-6-Bromo-1-[2-(tert-butoxycarbonylamino)propyl]-3-ethylindazole (S)-6-Bromo-1-[2-(tert-butoxycarbonylamino)propyl]-3-ethylindazole was prepared according to the method described in Example 2 using 6-bromo-3-ethylindazole (0.27 g, 1.2 mmol) to produce 0.26 g (61%) of the product as a white solid: IR $v_{max}$ (Nujol/cm$^{-1}$) 3354, 1681, 1536, 1461, 1371 and 1174; NMR $\delta_H$ (400 MHz, CDCl$_3$) 1.15 (3H, d, J 7 Hz), 1.35–1.43 (12H, m), 2.97 (2H, q, J 7.5 Hz), 4.03–4.13 (1H, m), 4.31–4.42 (2H, m), 4.79 (1H, br s), 7.20 (1H, dd, J 2, 9 Hz), 7.52 (1H, d, J 8.5 Hz) and 7.58 (1H, br s).

(S)-1-(6-Bromo-3-ethylindazol-1-yl)-2-propylamine Fumarate (S)-1-(6-Bromo-3-ethylindazol-1-yl)-2-propylamine fumarate was prepared according to the method described in Example 2 using (S)-6-bromo-1-[2-(tert-butoxycarbonylamino)propyl]-3-ethylindazole (0.6 g, 1.7 mmol) to produce 0.4 g (61% yield) of the title compound as a white solid: mp 148–150° C.; IR $v_{max}$ (Nujol/cm$^{-1}$) 1702, 1608, 1460, 1377, 1050, 975 and 651; NMR $\delta_H$ (400 MHz, CDCl$_3$) 1.13 (3H, d, J 6.5 Hz), 1.32 (3H, t, J 7.5 Hz), 2.93 (2H, q, J 7.5 Hz), 3.57 (1H, m), 4.35–4.52 (2H, m), 6.49 (2H, s), 7.25 (1H, dd, J 1.5, 8.5 Hz), 7.74 (1H, d, J 8 Hz) and 8.02 (1H, d, J 1.5 Hz).

Example 8

(S)-1-(3-Ethyl-6-methylthioindazol-1-yl)-2-propylamine Fumarate

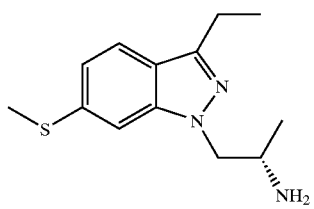

2'-Fluoro-4'-methylthiopropiophenone

To a stirred slurry of aluminium (III) chloride (3.3 g, 25 mmol) in chloroform (20 mL) under Ar at 0° C. was added dropwise over 20 min propionyl chloride (2.5 g, 27 mmol) while the temperature was maintained below 10° C. To the mixture was added portionwise 3-fluorothioanisole (3.0 g, 21 mmol) such that the temperature remained below 5° C.

The mixture was warmed to room temperature, stirred for 30 min, poured onto ice-water (100 mL) and extracted with chloroform (3×50 mL). The combined organic extracts were dried (magnesium sulfate) and concentrated in vacuo to give the product (3.8 g, 92%) as a pale yellow oil: NMR $\delta_H$ (400 MHz, CDCl$_3$) 1.19 (3H, t, J 7 Hz), 2.51 (3H, s), 2.96 (2H, m), 6.92 (1H, dd, J 2, 8 Hz), 7.03 (I1H. dd, J 2, 8 Hz) and 7.82 (1H, t, J 8 Hz).

2'-Fluoro-4'-methylthiophenylpropiohydrazone

2'-Fluoro-4'-methylthiophenylpropiohydrazone was prepared according to the method described in Example 5 using 2'-fluoro-4'-methylthiopropiophenone (3.3 g, 17 mmol) to produce 2.3 g (68%) of the product as a colourless oil: IR $v_{max}$ (Nujol/cm$^{-1}$) 3386, 1486, 1400, 1209, 891 and 818; NMR $\delta_H$ (400 MHz, CDCl$_3$) 1.06 (1H, t, J 7.5 Hz), 1.12 (2H, t, J 7.5 Hz), 2.48 (0.6H, q, J 7.5 Hz), 2.58 (1.4H, q, J 7.5 Hz), 5.06 (0.5H, br s), 5.45 (1.5H, br s), 6.89–7.13 (2.3H, m) and 7.38 (0.7H, t, J 8 Hz).

3-Ethyl-6-methylthio-1H-indazole

3-Ethyl-6-methylthio-1H-indazole was prepared according to the method described in Example 5 using 2'-fluoro-4'-methylthiophenylpropiohydrazone (2.0 g, 9.4 mmol) to produce 0.87 g (48%) of the product as a pale orange solid: IR $v_{max}$ (Nujol/cm$^{-1}$) 3169, 1618, 1463, 1300, 1046 and 783; NMR $\delta_H$ (400 MHz, CDCl$_3$) 1.44 (3H, t, J 7.5 Hz), 2.55 (3H, s), 3.03 (2H, q, J 7.5 Hz), 7.08 (1H, d, J 8.5), 7.28 (1H, s) and 7.6 (1H, d, J 8.5).

(S)-1-[2-(tert-Butoxycarbonylamino)propyl]-3-ethyl-6-methylthioindazole (S)-1-[2-(tert-Butoxycarbonylamino)propyl]-3-ethyl-6-methylthioindazole was prepared according to the method described in Example 2 using 3-ethyl-6-methylthio-1H-indazole (0.42 g, 2.2 mmol) to produce 1.1 g (69%) of the product as a white solid: IR $v_{max}$ (Nujol/cm$^{-1}$) 3354, 1681, 1512, 1459, 1368, 1250, 1172 and 786; NMR $\delta_H$ (400 MHz, CDCl$_3$) 1.13 (3H, d, J 7 Hz), 1.34–1.46 (12H, m), 2.57 (3H, s), 2.95 (2H, q, J 7.5), 4.04–4.15 (1H, m), 4.27–4.44 (2H, m), 4.93 (1H, br s), 7.03 (1H, d, J 8.5 Hz), 7.28 (1H, br s) and 7.55 (1H, d, J 9 Hz).

(S)-1-(3-Ethyl-6-methylthioindazol-1-yl)-2-propylamine Fumarate (S)-1-(3-Ethyl-6-methylthioindazol-1-yl)-2-propylamine fumarate was prepared according to the method described in Example 2 using (S)-1-[2-(tert-butoxycarbonylamino)propyl]-3-ethyl-6-methylthioindazole (0.45 g, 1.2 mmol) to produce 0.25 g (57% yield) of the title compound as a colourless solid: mp 147–149° C.; IR $v_{max}$ (Nujol/cm$^{-1}$) 1702, 1611, 1460, 1377, 1299, 1224, 971, 798 and 650; NMR $\delta_H$ (400 MHz, DMSO-d$_6$) 1.13 (3H, d, J 6.5 Hz), 1.31 (3H, t, J 7.5 Hz), 2.57 (3H, s), 2.89 (2H, q, J 7.5 Hz), 3.59 (1H, m), 4.35–4.56 (2H, m), 6.49 (2H, s), 7.01 (1H, dd, J 1.5, 8.5 Hz), 7.52 (1H, br s) and 7.66 (1H, d, J 8.5 Hz).

What is claimed is:

1. A chemical compound of formula (I):

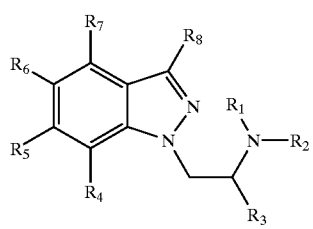

(I)

wherein:
R₁ to R₃ are independently selected from hydrogen and alkyl;
R₄ to R₇ are independently selected from hydrogen, halogen, hydroxy, alkyl, aryl, amino, monoalkylamino, dialkylamino, alkoxy, aryloxy, alkylthio, arylthio, arylsulfoxyl, arylsulfonyl, alkylsulfoxyl, alkylsulfonyl, nitro, cyano, carboxaldehyde, alkylcarbonyl, arylcarbonyl, aminocarbonyl, monoalkylaminocarbonyl, dialkylaminocarbonyl, alkoxycarbonylamino, aminocarbonyloxy, monoalkylaminocarbonyloxy, dialkylaminocarbonyloxy, monoalkylaminocarbonylamino and dialkylaminocarbonylamino; and
R₈ is selected from methyl, ethyl, propyl or butyl,
and pharmaceutically acceptable salts and prodrugs thereof.

2. A compound according to claim 1 wherein R₁ and R₂ are hydrogen.

3. A compound according to claim 1 wherein R₁ is hydrogen and R₂ is alkyl.

4. A compound according to claim 1 wherein R₁ is hydrogen and R₂ is arylalkyl.

5. A compound according to claim 1, wherein R₃ is alkyl.

6. A compound according to claim 1, wherein R₃ is methyl.

7. A compound according to claim 1 wherein one or more of R₄, R₅, R₆ and R₇ is/are hydrogen.

8. A compound according to claim 1 wherein R₄ is hydrogen.

9. A compound according to claim 1 wherein R₇ is hydrogen.

10. A compound according to claim 1 wherein one or more of R₄ to R₇ is selected from halogen.

11. A compound according to claim 1 wherein R₅ is halogen, alkoxy or alkylthio.

12. A compound according to claim 1 wherein R₆ is halogen or hydrogen.

13. A compound according to claim 1 wherein R₈ is alkyl.

14. A compound according to claim 1 to 12 wherein R₈ is methyl or ethyl.

15. A compound according to claim 1 which is selected from the group consisting of 1-(6-methoxy-3-methylindazol-1-yl)-2-propylamine, 1-(5,6-difluoro-3-methylindazol-1-yl)-2-propylamine, 1-(6-chloro-5-fluoro-3-methylindazol-1-yl)-2-propylamine, 1-(3-ethyl-6-trifluoromethylindazol-1-yl)-2-propylamine, 1-(6-bromo-3-ethylindazol-1-yl)-2-propylamine and 1-(3-ethyl-6-methylthioindazol-1-yl)-2-propylamine.

16. A method of treatment of disorders of the central nervous system; damage to the central nervous system; cardiovascular disorders; gastrointestinal disorders; diabetes insipidus, and sleep apnea comprising administering to a patient in need of such treatment an effective dose of a compound of formula (I) as set out in claim 1.

17. A method according to claim 16 wherein the disorders of the central nervous system are selected from the group consisting of depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addition, obesity, bulimia, anorexia nervosa and premenstrual tension.

18. A method according to claim 16 wherein the damage to the central nervous system is by trauma, stroke, neurodegenerative diseases, encephalitis, meningitis or toxic or infective CNS diseases.

19. A method according to claim 18 wherein said toxic or infective CNS disease is encephalitis or meningitis.

20. A method according to claim 16 wherein the cardiovascular disorder is thrombosis.

21. A method according to claim 16 wherein the gastrointestinal disorder is dysfunction of gastrointestinal motility.

22. A method according to claim 16 wherein said medicament is for the treatment of obesity.

23. A method according to claim 16 wherein said treatment is prophylactic treatment.

24. A pharmaceutical composition comprising a compound of formula (I) as set out in claim 1 in combination with a pharmaceutically acceptable carrier or excipient.

* * * * *